United States Patent [19]

Trivedi

[11] Patent Number: 5,747,528

[45] Date of Patent: May 5, 1998

[54] CHROMAN DERIVATIVES AS ANTI-OXIDANTS

[75] Inventor: Bharat Kakidas Trivedi, Farmington Hills, Mich.

[73] Assignee: Warner-Lambert Company, Morris Plains, N.J.

[21] Appl. No.: 788,534

[22] Filed: Jan. 24, 1997

[51] Int. Cl.$^6$ .................. C07D 311/04; A61K 31/35
[52] U.S. Cl. .................. 514/456; 549/407; 544/151; 514/233.5
[58] Field of Search .................. 549/407; 514/456, 514/233.5; 544/151

[56] References Cited

U.S. PATENT DOCUMENTS

| | | | |
|---|---|---|---|
| 4,360,532 | 11/1982 | Sundeen | 424/283 |
| 5,015,661 | 5/1991 | Walser | 514/443 |
| 5,055,598 | 10/1991 | Ohuchida et al. | 549/407 |
| 5,132,310 | 7/1992 | Walser | 514/302 |
| 5,169,957 | 12/1992 | Ohuchida et al. | 549/407 |
| 5,260,294 | 11/1993 | Walser | 514/230.5 |
| 5,266,709 | 11/1993 | Ohuchida et al. | 549/407 |
| 5,374,643 | 12/1994 | Atwal et al. | 514/364 |
| 5,380,747 | 1/1995 | Medford et al. | 514/423 |
| 5,384,414 | 1/1995 | Ohuchida et al. | 549/389 |
| 5,387,596 | 2/1995 | Takebayashi et al. | 514/369 |
| 5,508,450 | 4/1996 | Ohuchida et al. | 549/389 |

FOREIGN PATENT DOCUMENTS

| | | |
|---|---|---|
| 0640609 | 3/1995 | European Pat. Off. . |
| 2215778A | 8/1990 | Japan . |
| 1296431 | 11/1972 | United Kingdom . |
| 950609 | 3/1995 | WIPO . |

OTHER PUBLICATIONS

Faruqi and DiCorleto, *Br. Heart J.*, 1993, 69(Suppl.):s19–s29.

Ross *Nature*, 1993, 362:801–809.

Li et al., *Arteriosclerosis Throm.*, 1993, 13(2):197–204.

O'Brien et al., *J. Clin. Invest.*, 1993, 92:945–951.

Collins, *Lab. Invest.*, 1993, 68(5):499–508.

Tanaka et al., *Circulation*, 1993, 88(4)Part 1:1788–1803.

Marui et al., *J. Clin. Invest.*, 1993, 92:1866–1874.

Pelletier et al., *J. Immunol.*, 1992, 149(7):2473–2481.

Pryor et al., *J. Org. Chem.*, 1993, 58(13):3521–3532.

Yoshioka et al., *J. Med. Chem.*, 1989, 32(2):421–428.

*Primary Examiner*—Zinna Northington-Davis
*Attorney, Agent, or Firm*—Elizabeth M. Anderson

[57] ABSTRACT

Chroman derivatives of Formula I or a pharmaceutically acceptable salt thereof are inhibitors of VCAM-1 and ICAM-1 and are thus useful in the treatment of inflammation, atherosclerosis, restenosis, and immune disorders such as arthritis and transplant rejection

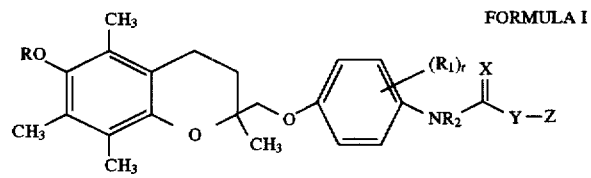

FORMULA I wherein:

R=Hydrogen or phenyl;

$R_2$=Hydrogen or lower alkyl of from 1-4 carbon atoms;

X=Oxygen or Sulfur;

Y=$(CH_2)_n$, —NR' where R' is hydrogen, alkyl of from 1 to 12 carbon atoms or aryl of from 6 to 10 carbon atoms, or Z; and Z is an alkyl or aryl containing moiety.

19 Claims, No Drawings

CHROMAN DERIVATIVES AS ANTI-OXIDANTS

This application claims the benefit of U.S. Provisional Application Number 60/012,023 filed Feb. 21, 1996.

FIELD OF THE INVENTION

The present invention relates to novel compounds and medical methods of treatment of inflammation, atherosclerosis, restenosis, and immune disorders such as arthritis and transplant rejection. More particularly, the present invention concerns the use of chroman derivatives.

BACKGROUND OF THE INVENTION

Vascular cell adhesion molecule 1 (VCAM-1) is inducible by cytokines on endothelial cells and on a more restricted subset of nonvascular cells than ICAM-1 (Bevilacqua, 1993). A single VCAM-1 gene gives rise through alternative splicing to distinct isoforms that differ in the number of integrin-binding sites (Vonderheide and Springer, 1992; Osborn et al. 1992; Moy et al., 1993; VCAM-1 is a ligand for the integrin α4β1 (VLA-4) and binds weakly to αβ7 (R üegg et al., 1992; Chan et al. 1992)

Adhesion of monocytes to vascular endothelium represents an early event in pathologies involving chronic inflammation. These include atherosclerosis, restenosis, and immune disorders like arthritis and transplant rejection. The adhesion of monocytes to endothelium is mediated by expression of cell-surface molecules on endothelial cells. These adhesion molecules are vascular cell adhesion molecule-1 (VCAM-1), intracellular adhesion molecule-1 (ICAM-1), and E-selectin. Of these three adhesion molecules, VCAM-1 seems to be involved in binding monocytes (Faruqi R. M., and Di Corleto P. E., Br. Heart J., 1993;69:s19–s29).

Atherosclerosis is viewed as a chronic inflammatory disease of the artery involving monocyte accumulation, smooth muscle proliferation, and cholesteryl ester accumulation by both these cell types. Monocyte accumulation in atherosclerosis begins with the adherence of blood-borne monocytes to defined areas of aortic endothelium (Ross R., Nature, 1993;362:801–809). The attachment of monocytes is mediated by VCAM-1 expression on endothelial cell-surface as suggested by studies in animal models of atherosclerosis (Li H., et al., Arteriosclerosis Throm., 1993;13:197–204) as well as the expression of VCAM-1 in human atherosclerotic lesions (O'Brien K. D., et al., J. Clin. Invest., 1993;92:945–951). Once the monocytes bind to the endothelium, they migrate into the subendothelial space and transform into cholesteryl ester loaded "foam cells." Monocyte derived foam cells secrete a variety of cytokines, growth factors, and proteases which promote atherosclerotic lesion formation and growth. Therefore, inhibiting the binding of monocytes to VCAM-1 may block monocyte recruitment and lesion formation (Collins T., Lab. Invest., 1993;68:499–508). Selective inhibition of VCAM-1 functions will also decrease nonspecific effects on inflammation.

Intimal thickening response in the artery known as restenosis, following balloon angioplasty is a common and frequent complication that leads to occlusion of coronary vessels. After balloon injury, the endothelial cells regenerate and express VCAM-1 at the surface. This expression of VCAM-1 could contribute to leukocyte recruitment and immune activation in restenosis (Tanaka H., et al., Circulation, 1993;88:1788–1803). Therefore, inhibitors of VCAM-1 expression may be therapeutically useful in restenosis.

Monoclonal antibodies to VCAM-1 have been disclosed by other investigators for therapeutic utility in atherosclerosis. Similarly, pyrrolidine thiocarbamate (PDTC) and two of its analogs which inhibit VCAM-1 expression in vitro (Marui, et al., J. Clin. Invest., 1993;91:1866–1874 and U.S. Pat. No. 5,380,747) have been disclosed for the treatment of atherosclerosis, postangioplasty restenosis, and inflammation. The potential utility of VCAM-1 inhibitors in heart transplant rejection was reported in studies which demonstrated that monoclonal antibodies to VCAM-1 markedly reduced the rejection of transplanted hearts in a rat model and improved the survival rate of these animals (Pelletier R. P., et al., J. Immunol., 1992;149:2473–2481).

Some natural and synthetic antioxidants are described in Journal of Organic Chemistry 58:3521–3532, 1993. An amino phenoxy chroman reactant is disclosed at p. 3522. See also Yoshioka, T. et al. J. Med. Chem. 1989, 32:421–428.

We have surprisingly and unexpectedly found that chroman derivatives are inhibitors of VCAM-1 and ICAM-1 and are thus useful as agents for the treatment of inflammation, atherosclerosis, restenosis, and immune disorders such as arthritis and transplant rejection.

SUMMARY OF THE INVENTION

Accordingly, a first embodiment of the present invention provides a method of treatment of inflammation, atherosclerosis, restenosis, immune disorders; and transplant rejection in mammals in need thereof comprising administering to such mammal an effective amount of a chroman of Formula I or a pharmaceutically acceptable salt thereof:

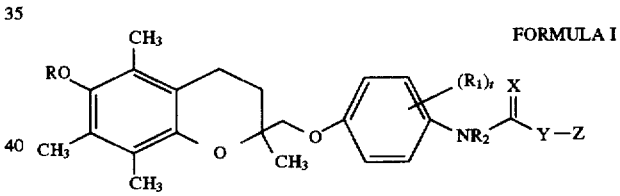

FORMULA I wherein:

R=Hydrogen or —$CH_2$-phenyl;

$R_2$=Hydrogen or lower alkyl of from 1–4 carbon atoms;

X=Oxygen or Sulfur;

Y=$(CH_2)_n$ or —NR' where R' is hydrogen, alkyl of from 1 to 12 carbon atoms or aryl from 6 to 10 carbon atoms, or Z;

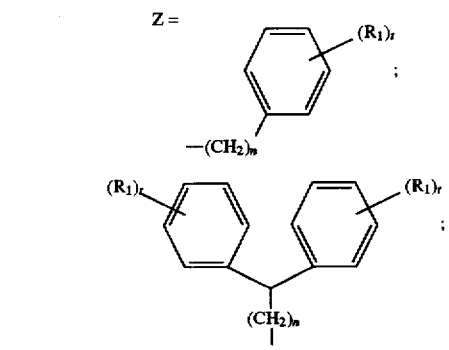

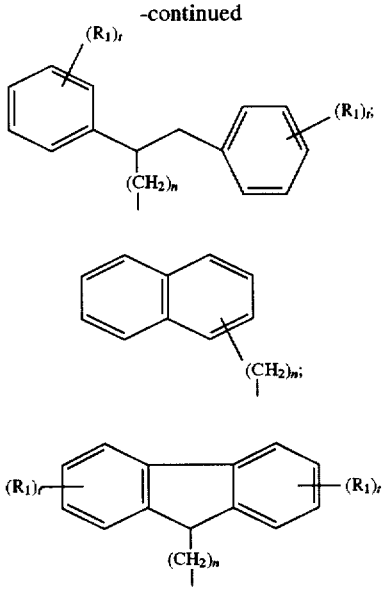

or $(CH_2)_n$—alkyl of from 1 to 12 carbon atoms;
wherein n=0, 1 or 2;
t=0, 1, 2 or 3; and
$R_1$ is:
  alkyl of from 1 to 4 carbon atoms, hydroxy,
  alkoxy of from 1 to 4 carbon atoms, halogen,
  —$CF_3$,
  —CN,
  —$NH_2$,
  —$N(CH_3)_2$,
  —$CH_2N(CH_3)_2$,
  —COOH,
  —COO alkyl of from 1 to 4 carbon atoms,
  —$CH_2NH$—$C(CH_3)(CH_2OH)_2$,
  —$CH_2$—Morpholine,
  —$OCH_2$—$CO_2CH_3$,
  —$OCH_2$—$CO_2C_2H_5$, or
  —$O(CH_2)_2$—$N(C_2H_5)$ A still further embodiment of the present invention is a method of treatment of inflammation, atherosclerosis in mammals in need thereof comprising administering to such mammal an effective amount of a compound selected from the group consisting of: chroman of formula I in combination with one or more agents-selected from the group consisting of:

(a) ACAT inhibitor;

(b) HMG-CoA reductase inhibitor;

(c) Lipid regulator; and (d) Bile acid sequestrant;

or a pharmaceutically acceptable salt thereof.

Also, the invention is directed to novel compounds, which are some of the compositions of Formula I.

Finally, the present invention is directed to a pharmaceutical composition for administering an effective amount of a compound of Formula I in unit dosage form in the treatment methods mentioned above.

DETAILED DESCRIPTION OF THE INVENTION

In the compounds of Formula I, the term "lower alkyl" means a straight or branched hydrocarbon radical having from 1 to 4 carbon atoms and includes, for example, methyl, ethyl, n-propyl, isopropyl, n-butyl, sec-butyl, isobutyl, tert-butyl and the like.

The term "lower alkoxy" is O-alkyl as defined above for alkyl. "Halogen" is fluorine, chlorine, bromine, or iodine.

The term "mammal" includes animals and humans.

Some of the compounds of Formula I are capable of further forming both pharmaceutically acceptable acid addition and/or base salts. All of these forms are within the scope of the present invention.

Pharmaceutically acceptable acid addition salts of the compounds of Formula I include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M., et al., "Pharmaceutical Salts," *J. Pharma. Sci.*, 1977;66:1).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see Berge, Supra, 1977).

The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R(D) or S(L) configuration. The present invention includes all enantiomeric and epimeric forms as well as the appropriate mixtures thereof.

A preferred compound of the first embodiment used in the method of the present invention is a compound of formula I:

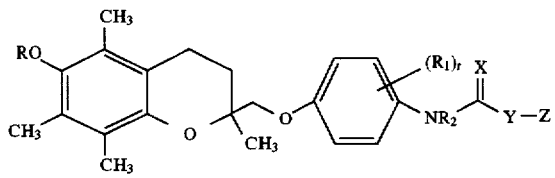

wherein:

R=Hydrogen or —CH$_2$— phenyl;

R$_2$=Hydrogen or lower alkyl of from 1–4 carbon atoms;

X=Oxygen or Sulfur;

Y=(CH$_2$)$_n$ or —NR' where R' is hydrogen or lower alkyl of from 1 to 4 carbon atoms, or Z;

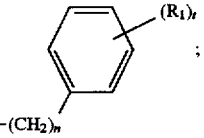

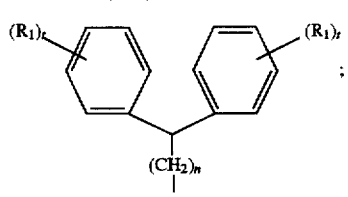

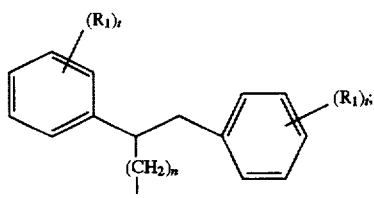

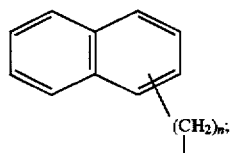

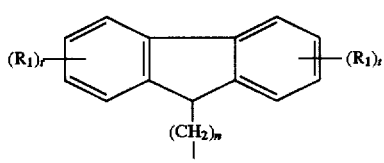

or —(CH$_2$)$_n$—alkyl of from 1 to 12 carbon atoms;

wherein n=0, 1 or 2;

t=0, 1, 2 or 3; and

R$_1$ is:

alkyl of from 1 to 4 carbon atoms, hydroxy,
alkoxy of from 1 to 4 carbon atoms, halogen,
—CF$_3$,
—CN,
—NH$_2$,
—N(CH$_3$)$_2$,
—CH$_2$N(CH$_3$)$_2$,
—COOH,
—COO alkyl of from 1 to 4 carbon atoms,
—CH$_2$NH—C(CH$_3$) (CH$_2$OH)$_2$,
—CH$_2$-Morpholine,
—OCH$_2$—CO$_2$CH$_3$,
—OCH$_2$—CO$_2$C$_2$H$_5$, or
a pharmaceutically acceptable salt of a compound of Formula I.

Preferred compounds used in the second embodiment of the present invention include one or more agents selected from the group consisting of an acyl CoA:cholesterol acyltransferase (ACAT) inhibitor; 3-hydroxy-3-methyglutaryl-coenzyme A reductase (HMG-CoA reductase) inhibitor; lipid regulator; and bile acid sequestrant.

Examples of ACAT inhibitors include DL-melinamide disclosed in British Patent 1,123,004 and Japan. J. Pharmacol., 1986;42:517–523; 2,2-dimethyl-N-(2,4,6-trimethoxyphenyl)dodecanamide disclosed in U.S. Pat. No. 4,716,175; N-[2,6-bis(1-methylethyl)phenyl]—N'-[[1-(4-dimethylaminophenyl)cyclopentyl]methyl]urea disclosed in U.S. Pat. No. 5,015,644; 2,6-bis(1-methyl-ethyl)phenyl[[2,4,6-tris(1-methylethyl)phenyl]-acetyl]sulfamate disclosed in copending U.S. patent application Ser. No. 08/233,932 filed Apr. 13, 1994; and the like. U.S. Pat. Nos. 4,716,175 and 5,015,644 and U.S. patent application Ser. No. 08/233,932 and British Patent 1,123,004 and Japan. J. Pharmacol., 1986;42:517–523 are hereby incorporated by reference.

Examples of HMG—CoA reductase inhibitors include lovastatin disclosed in U.S. Pat. No. 4,231,938; pravastatin disclosed in U.S. Pat. No. 4,346,227; simvastatin disclosed in U.S. Pat. No. 4,444,784; fluvastatin disclosed in U.S. Pat. No. 4,739,073; atorvastatin disclosed in U.S. Pat. Nos. 4,681,893 and 5,273,995; and the like. U.S. Pat. Nos. 4,231,938, 4,346,227, 4,444,784, 4,681,893, 4,739,073, and 5,273,995 are hereby incorporated by reference.

Examples of bile acid sequestrants include colestipol disclosed in U.S. Pat. Nos. 3,692,895 and 3,803,237; cholestyramine disclosed in U.S. Pat. No. 3,383,281 and Casdorph R. in Lipid Pharmacology., 1976;2:222–256, Paoletti C., Glueck J., eds. Academic Press, NY; and the like. U.S. Pat. Nos. 3,692,895, 3,803,237, and 3,383,281 and R. Casdorph, supra, 1976, are hereby incorporated by reference.

Examples of lipid regulators include gemfibrozil described in U.S. Pat. No. 3,674,836; bezafibrate disclosed in U.S. Pat. No. 3,781,328; clofibrate disclosed in U.S. Pat. No. 3,262,850; fenofibrate disclosed in U.S. Pat. No. 4,058,552; niacin disclosed in McElvain, et al., Org. Syn., 1925;4:49; and the like. U.S. Pat. Nos. 3,674,836, 3,781,328, 3,262,850, and 4,058,552 and McElvain, et al., Org. Syn., 1925;4:49 are hereby incorporated by reference.

Methods of preparing ACAT inhibitors, HMG-CoA reductase inhibitors, lipid regulators, and bile acid sequestrants used in the second embodiment of the present invention are disclosed in the aforementioned references.

General Synthesis:

Compounds of Formula I can be synthesized by reacting the aniline derivative (Formula II, R=H) by first hydrogenolysis of the benzylether followed by reaction with an appropriate isothiocyanate or acid chloride in an aprotic solvent such as THF, dichloromethane or preferably acetonitrile at 0° C. to a reflux temperature, preferably at room temperature. The title compounds (I,R=H) can also be prepared by reversing the order of reaction sequence shown:

anti-mouse IgG+IgM, F(ab)2 fragments {1:1000 dilution} for 1 hour at room temperature. The second antibody was then aspirated and cells washed 3 times. [125I]Streptavidin

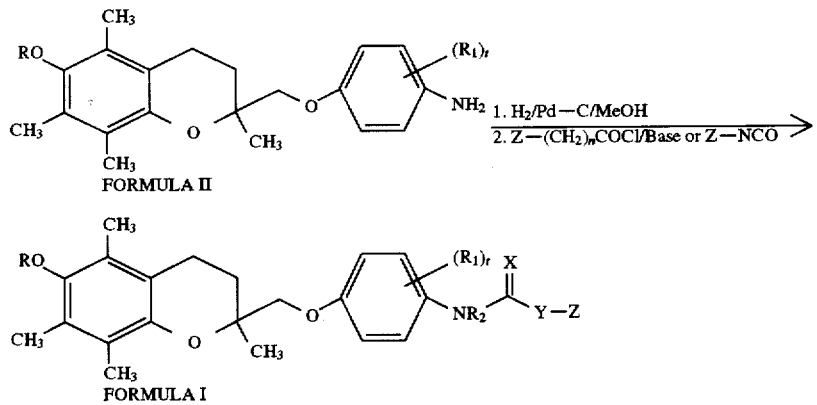

Wherein: R, $R_2$, X, Y, $R_1$, Z, n and t are as defined above.

The chromans are valuable agents for the treatment of inflammation, atherosclerosis, restenosis, and immune disorders such as arthritis and transplant rejection. The tests employed indicate that the compounds possess activity against VCAM-1 and ICAM-1.

IMMUNOASSAYS FOR DETECTION OF CELL-SURFACE ADHESION MOLECULES VCAM-1 AND ICAM-1

MATERIALS:

CELL CULTURE: Human aortic endothelial cells (CellSystem) Media: 50:50 mix of CS 3.0 (CellSystem) and MCDB-107 (Sigma) 10% fetal bovine serum (FBS) (Hyclone) Tissue culture plates (24 well) (Costar) TNF: recombinant Tumor necrosis factor-alpha (Genzyme)

IMMUNOASSAYS: 10% buffered Formalin (Baxter) Dulbecco's modified eagle medium (DMEM), Phosphate buffered saline (PBS) (Gibco) Bovine serum albumin (BSA) (Sigma) Anti-ICAM-1 antibody (R&D System, BBA#3) Sheep anti-mouse IgG (Cappel, #55558) Horseradish peroxidase (HRP)-KIT (Bio-Rad, #172-1064) Anti-VCAM-1 antibody (R&D System, BBA#6) Goat anti-mouse IgG+IgM, F(ab)2 fragments, biotin conjugated (Jackson Immuno Research Lab, #115-066-068) 125-I-Streptavidin (Amersham, #IM.236)

METHODS:

Human aortic endothelial cells (HAEC) were seeded at 100,000 cells/mL/well in 24 well cluster plates and placed in a 5% $CO_2$ to 95% $O_2$ humidified incubator at 37° C. At confluence (typically after 24 hours), the cells were incubated with TNF (250 U/mL) in the presence or absence of compounds at indicated concentrations (dissolved in dimethylsulfoxide (DMSO), 0.005% final DMSO concentration) overnight (18 hours) in the humidified incubator. After this incubation, media was removed, cells washed 3 times with PBS, and fixed for 15 minutes with 10% buffered formalin at room temperature. After removal of formalin, cells were washed 3 times with 2% BSA-DMEM and then processed separately for VCAM-1 or ICAM-1 cell-surface detection as described below.

VCAM-1 ASSAY

The cells were incubated with anti-VCAM-1 monoclonal antibody (1.25 µg/mL) for 2 hours at 37° C. The unbound antibody was aspirated, cells washed 3 times with 2% BSA-DMEM and incubated with biotin conjugated Goat anti-mouse IgG+IgM, F(ab)2 fragments {1:1000 dilution} for 1 hour at room temperature. The second antibody was then aspirated and cells washed 3 times. [125I]Streptavidin (1:60 dilution) was added and cells incubated for 15 minutes at 4° C. Cells were washed again (4 times) and digested overnight with the addition of 500 µL of 1N NaOH and radioactivity contained in the digests counted. Cell-surface VCAM-1 expression is shown as radioactivity bound to the cell surface under various conditions.

ICAM-1 ASSAY

Anti-ICAM-1 monoclonal antibody (0.5 µg/mL) was added to the cells and incubated for 2 hours at 37° C. The media was aspirated, cells washed 4 times with 2% BSA-DMEM, and second antibody added (sheep anti-mouse IgG, 1:3000 dilution), and cells incubated for 1 hour at 37° C. After removal of the unbound antibody and 4 washes with DMEM alone, the cells were incubated with the HRP color reagent for 15 minutes at 37° C. in the dark. Fifty microliters of the color reagent from each well was transferred to 96 well plates and absorbance read at 414 nm on a Titertek ELISA reader. Cell-surface ICAM-1 expression is presented as $OD_{414}$.

The data in the table show the VCAM-1 activity of representative phenoxy chromans of the present invention.

TABLE 1

Biological Activity

| Example | Compound | VCAM-1 ($IC_{50} = \mu M$) |
|---|---|---|
| 1 | 1-Benzhydryl-3-[4-(6-hydroxy, 2,5,7,8-tetramethyl-chroman-2-ylmethoxy)-phenyl]-thiourea | 23.1 |

The chroman derivatives of the present invention may have an ability to block leukocyte adhesion in a rat model.

It has been established for some time that the attachment and migration of bloodborne monocytes across aortic endothelial cells is among the initial events in the development of the atherosclerotic plaques (Faruqi R. M. and Dicorleto P. E., "Mechanisms of Monocyte Recruitment and Accumulation," British Heart J., 1993;69(Supp):S19–S29). This animal model assesses the effect of compounds of the present invention on the recruitment of leukocytes into vascular tissue. The animal model is based on the fact that only polymorphonuclear neutrophils and monocytes possess the enzyme myeloperoxidase. The accumulation of enzyme in the lungs is dependent on an up regulation of various adhesion molecules. Histopathological analysis has demonstrated that a majority of the cells in the lungs at 24 hours are monocytes.

PROTOCOL

Male Sprague-Dawley rats weighing approximately 300 to 350 g, were obtained from Charles River, Portage, Mich. Test compounds were suspended in 0.5% methylcellulose and were administered by gavage on a milligram active drug moiety per kilogram body weight basis at 100 mg/kg. Glucan was suspended in sterile saline for injection at a concentration of 3.3 µg/µL. Three hundred microliter is injected in the penile vein. Two experiments were performed using three animals in three groups of control, glucan alone, and glucan and compound. Animals were dosed 18 hours before and concurrent with the glucan injection. At 4 and 24 hours, the hearts and lungs are removed and washed 3 times in normal saline solution. The lungs and hearts are placed in separate tubes containing 3 mL of a solution of normal saline containing 1 mg/mL of aprotinin and phenylmethyl sulfonyl fluoride (PMSF). The tissue is then homogenized using a polytron on the high setting. All samples are held on ice. The samples are then aliquoted and frozen at 20° C. The myeloperoxidase assay was standardized with the linear portion of the curve identified. Lowry protein assays were performed and the samples were diluted to obtain optical densities in the linear range. To 10 parts of a 0.1M sodium citrate buffer (pH=5.5) is added one part of a solution 0.1% o-dianisidine in absolute ethanol and one part of a 1 mM hydrogen peroxide solution. To this working solution is added 100 µL of the diluted protein homogenate solution. The reaction is stopped after 1 minute by the addition of 1 mL of 35% perchloric acid. All reactions were run in triplicate. The absorbance at 460 nm is then measured on a Beckman DU-70 spectrophotometer.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or Formula II or a corresponding pharmaceutically acceptable salt of a compound of Formula I or Formula II.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from 5% or 10% to about 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 200 mg preferably 0.5 mg to 100 mg according to the particular application and the potency of the active component. The composition can, if desired, also contain other compatible therapeutic agents.

In therapeutic use as agents for the treatment of atherosclerosis, restenosis, and immune disorders such as arthritis and transplant rejection, the compounds utilized in the pharmaceutical methods of this invention are administered at the initial dosage of about 0.01 mg to about 200 mg/kg daily. A daily dose range of about 0.01 mg to about 50 mg/kg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The ACAT inhibitors, HMG-CoA reductase inhibitors, lipid regulators, and bile acid sequestrants utilized in the second embodiment of the present invention are used in standard dosage amounts known in the art.

As further exemplification of the invention listed below are preferred embodiments wherein all parts are parts by weight and all temperatures are degrees Centigrade unless otherwise indicated.

EXAMPLE 1

1-Benzhydryl-3-[4-(6-hydroxy-2,5,7,8-tetramethyl-Chroman-2-ylmethoxy)-phenyl]-thiourea The aniline derivative (Formula II, R=—CH$_2$-phenyl) (25g) was dissolved in methanol (600 mL) and subjected to hydrogenolysis in the presence of a catalyst (20% Pd/C) at room temperature for 4 hrs. Catalyst was filtered, washed with methanol, and the solvent was removed from the filtrate under reduced pressure. Solid obtained was suspended in 150 mL of ether. It was filtered and dried yielding 17.7 gm (90%) of the aniline derivative (Formula II,R=H) having a melting point of 146–148° C.

Anal Calcd for C$_{20}$H$_{25}$NO$_3$:

Calcd: C=73.37; H=7.70, N=4.28

Found: C=73.11; H=7.52, N=4.21

The aniline derivative (II,R=H)(17.5 gg; 0.053 mole) was suspended in acetonitrile (750 mL). The suspension was slightly heated to make a homogeneous solution. A solution of benzhydrylisothioocyanate (24.3 g; 0.105 mole) was slowly added to this solution over a period of 30 mins. The clear homogeneous solution was stirred at room temperature for 20 hrs. Precipitated solid was filtered, washed with acetonitrile and dried yielding 28.2 gm (94%) of the title compound having a melting point of 179°–181° C.

Anal Calcd for C$_{34}$H$_{36}$N$_2$O$_3$S:

Calcd: C=73.88; H=6.56; N=5.07; S=5.80

Found: C=73.58; H=6.71; N=5.05; S=5.95

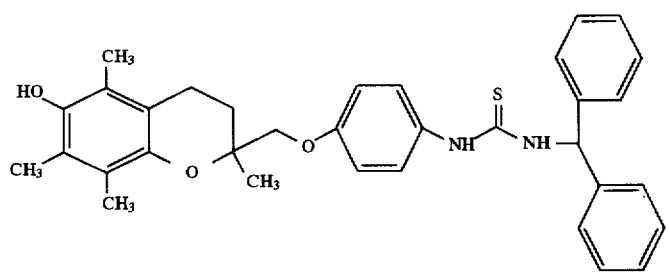

Following a similar synthesis of the above example, the following chromans were prepared:

| Example # | Name of Compound | Melting Point |
|---|---|---|
| 2 | 1-tert-Butyl-3-[4-(4-hydroxy-2,5,7,8-tetramethyl-chroman-2-ylmethoxy)-phenyl]-thiourea | 70–80° C. |
| 3 | 1-[4-(6-Hydroxy-2,5,7,8-tetramethyl-chroman-2-ylmethoxy)-phenyl]-3-naphthalen-2-yl-thiourea | 103–107° C. |
| 4 | 1-Benzhydryl-3-[4-(6-hydroxy-2,5,7,8-tetramethyl-chroman-2-ylmethoxy)-phenyl]-urea | 209–211° C. |

| Example # | Name of Compound | Melting Point |
|---|---|---|

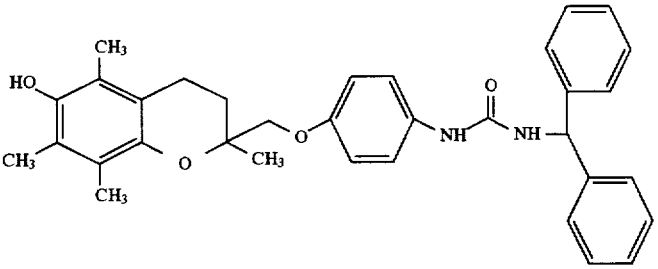

| 5 | 1-Dodecyl-3-[4-(6-hydroxy-2,5,7,8-tetramethyl-chroman-2-ylmethoxy)-phenyl]-thiourea | 72–75° C. |

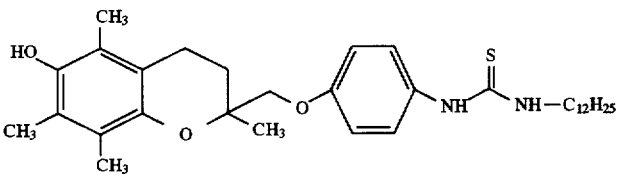

| 6 | 1-Benzyl-3-[4-(6-hydroxy-2,5,7,8-tetramethyl-chroman-2-ylmethoxy)-phenyl]-thiourea | 72–79° C. |

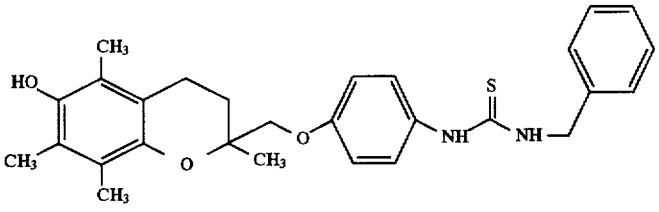

| 7 | 1-Benzhydryl-3-[4-(6-benzyloxy-2,5,7,8-tetramethyl-chroman-2-ylmethoxy)-phenyl]-thiourea | 171–173° C. |

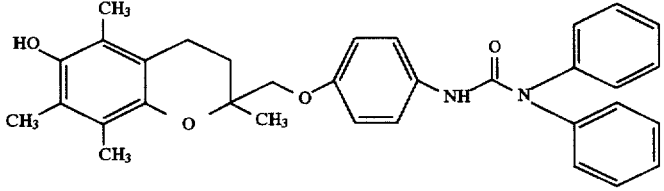

| 8 | 3-[4-(6-hydroxy-2,5,7,8-tetramethyl-chroman-2-ylmethoxy)-phenyl]-1,1diphenyl-urea | 80–90° C. |

| 9 | 1-(1,2-Diphenyl-ethyl)-3-[4-(6-hydroxy-2,5,7,8-tetramethyl-chroman-2-ylmethoxy)-phenyl]-thiourea | 90–95° C. |

| Example # | Name of Compound | Melting Point |
|---|---|---|

-continued

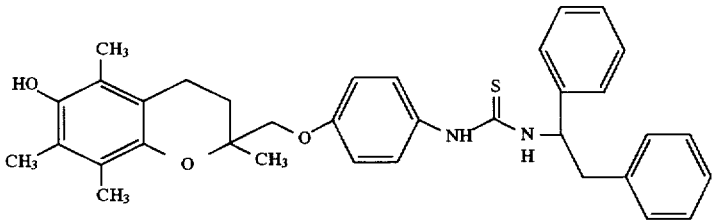

| 10 | 1-[4-(6-Hydroxy-2,5,7,8-tetramethyl-chroman-2-ylmethoxy)-phenyl]-3-(phenyl-p-tolyl-methyl)-thiourea | 173–176° C. |

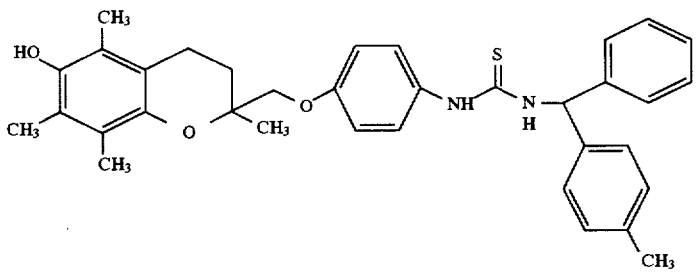

| 11 | 1-[4-(6-Hydroxy-2,5,7,8-tetramethyl-chroman-2-ylmethoxy)-phenyl]-3-(isopropyl-phenyl)-thiourea | 164–166° C. |

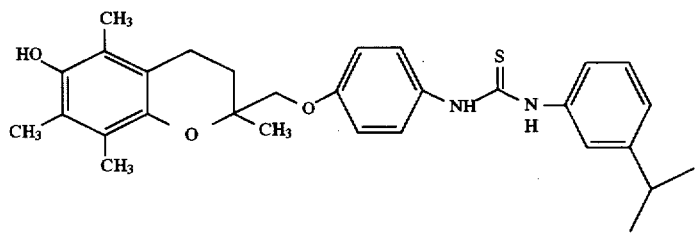

| 12 | 1-(2,2-Diphenyl-ethyl)-3-[4-(6-hydroxy-2,5,7,8-tetramethyl-chroman-2-ylmethoxy)-phenyl]-thiourea | 172–174° C. |

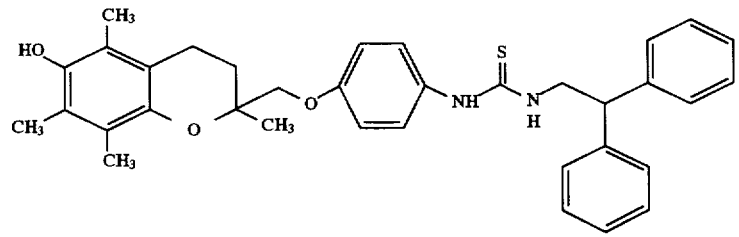

| 13 | 1-[(4-Chloro-phenyl)-phenyl-methyl]-3-[4-(6-hydroxy-2,5,7,8-tetramethyl-chroman-2-ylmethoxy)-phenyl]-thiourea | 85–90° C. |

| Example # | Name of Compound | Melting Point |
|---|---|---|
| 14 | 1-[4-(6-Hydroxy-2,5,7,8-tetramethyl-chroman-2-ylmethoxy)-phenyl]-3-(3-methoxy-phenyl)-thiourea | 143–145° C. |
| 15 | N-[4-[(3,4-dihydro-6-hydroxy-2,5,7,8-tetramethyl-[-2H-1-benzopyran-2-yl)methoxy]phenyl]-N'-(2-methoxyphenyl)urea | 82–92° C. |
| 16 | N-[4-[[3,4-dihydro-2,5,7,8-tetramethyl-6-(phenylmethoxy)-2H-1-benzopyran-2-yl]methoxy]phenyl]-N'-[2-(1,1-dimethylethyl)-6-methyl-phenyl]urea | 189–191° C. |
| 17 | N-[4-[3,4-dihydro-6-hydroxy-2,5,7,8-tetramethyl-2H-1-benzopyran-2-yl]methoxy]phenyl]-N'-[2-(1,1-dimethylethyl)-6-methylphenyl]urea | 190–192° C. |

-continued

| Example # | Name of Compound | Melting Point |
|---|---|---|
| 18 | 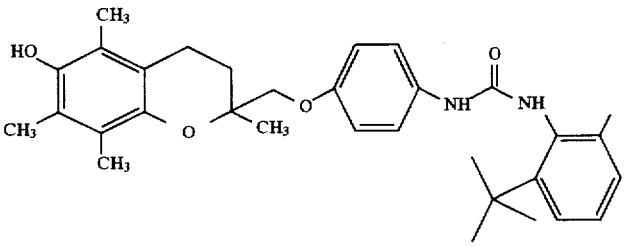 N-[2,6-bis(1-methylethyl)phenyl]-N'-[4-[(3,4-dihydro-6-hydroxy-2,5,7,8-tetramethyl-2H-1-benzopyran-2-yl)methoxy]phenyl]urea | 194–196° C. |
| 19 | 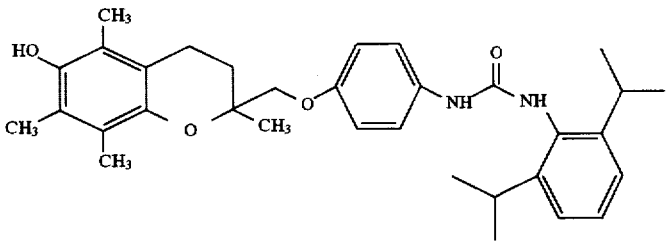 N-[4-[[3,4-dihydro-6-hydroxy-2,5,7,8-tetra-methyl-2H-1-benzopyran-2-yl)methoxy]phenyl]-N'-methylthiourea | 185–187° C. |
| 20 | 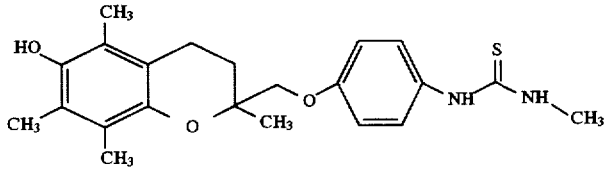 N-[4-[[3,4-dihydro-2,5,7,8-tetra-methyl-6-(phenylmethoxy)-2H-1-benzopyran-2-yl]methoxy]phenyl]-N'-[2-(1-methylethyl)phenyl]urea | 162–164° C. |
| 21 | 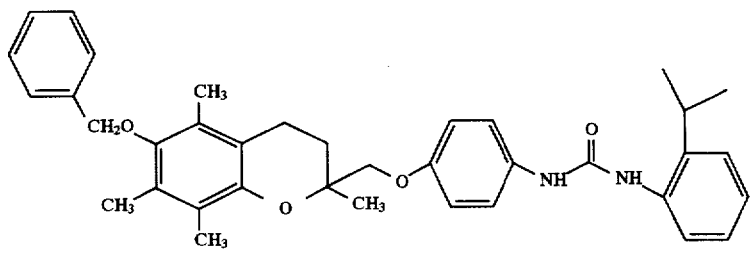 N-[4-(3,4-dihydro-6-hydroxy-2,5,7,8-tetramethyl-2H-1-benzopyran-2-yl)methoxy]phenyl]-N'-[2-(1-methylethyl)phenyl]urea | 112–120° C. |

While the forms of the invention herein disclosed constitute presently preferred embodiments, many others are possible. It is not intended herein to mention all of the possible equivalent forms or ramifications of the invention. It is understood that the terms used herein are merely descriptive rather than limiting and that various changes may be made without departing from the spirit or scope of the invention.

I claim:

1. A method for the treatment of inflammation, atherosclerosis, restenosis, immune disorders, and transplant rejection in mammals in need thereof comprising administering to such mammal an effective amount of a compound of Formula I

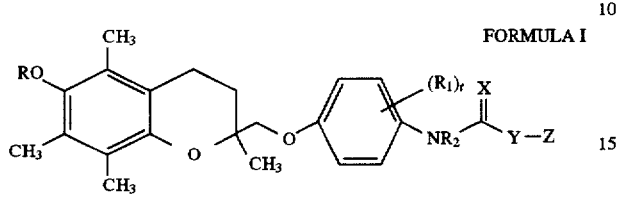
FORMULA I wherein:

R=Hydrogen or —CH$_2$— phenyl;

R$_2$=Hydrogen or lower alkyl of from 1–4 carbon atoms;

X=Oxygen or Sulfur;

Y=(CH$_2$)$_n$ or —NR' where R' is hydrogen, alkyl of from 1 to 12 carbon atoms or aryl of from 6 to 10 carbon atoms, or Z;

Z=

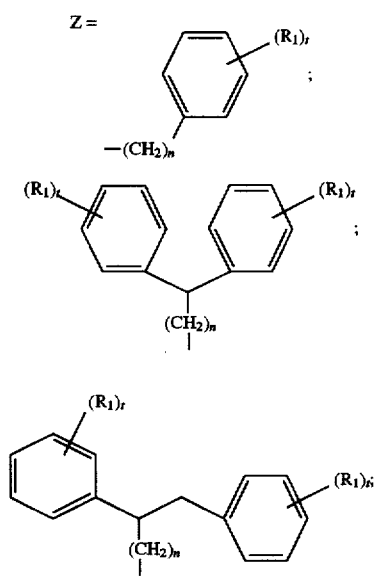

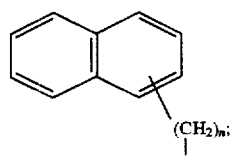

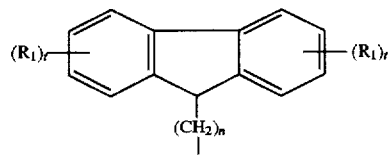

or —(CH$_2$)$_n$ alkyl of from 1 to 12 carbon atoms;

wherein n=0, 1 or 2;

t=0, 1, 2 or 3; and

R$_1$ is:

alkyl of from 1 to 4 carbon atoms, hydroxy, alkoxy of from 1 to 4 carbon atoms, halogen,

—CF$_3$,

—CN,

—NH$_2$,

—N (CH$_3$)$_2$,

—CH$_2$N (CH$_3$)$_2$,

—COOH,

—COO Alkyl of from 1 to 4 carbon atoms

—CH$_2$NH—C (CH$_3$) (CH$_2$OH)$_2$,

—CH$_2$—Morpholine,

—OCH$_2$—CO$_2$CH$_3$,

—OCH$_2$—CO$_2$C$_2$H$_5$, or

—O(CH$_2$)$_2$—N (C$_2$H$_5$)

or a pharmaceutically acceptable salt thereof.

2. The method of claim 1, wherein in a compound of Formula I, R is hydrogen.

3. The method of claim 1 wherein X is sulfur.

4. The method of claim 1 wherein t is zero.

5. The method of claim 1 wherein the Formula I compound is:

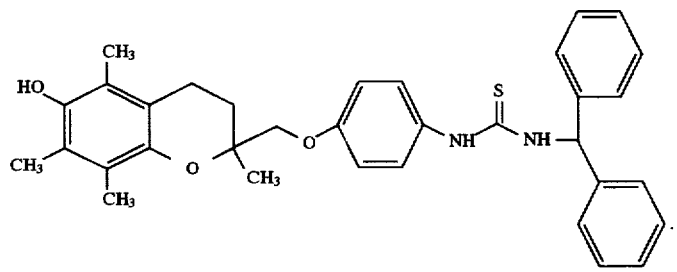

6. A method for the treatment of atherosclerosis in mammals in need thereof comprising administering to such mammal an effective amount of a compound of Formula I

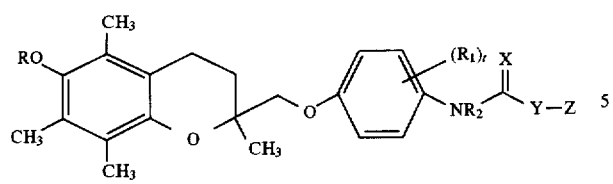

wherein:

R=Hydrogen or —CH$_2$— phenyl;

R$_2$=Hydrogen or lower alkyl of from 1–4 carbon atoms;

X=Oxygen or Sulfur;

y=(CH$_2$)$_n$, —NR' where R' is hydrogen, alkyl of from 1 to 12 carbon atoms or aryl of from 6 to 10 carbon atoms, or Z;

Z =

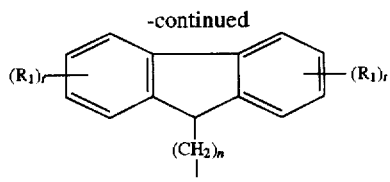

or —(CH$_2$)$_n$—alkyl of from 1 to 12 carbon atoms;

wherein n=0, 1 or 2, t=0, 1, 2 or 3; and

R$_1$ is:

alkyl of from 1 to 4 carbon atoms, hydroxy, alkoxy of from 1 to 4 carbon atoms, halogen,

—CF$_3$,

—CN,

—NH$_2$,

—N(CH$_3$)$_2$,

—N(CH$_3$)$_2$,

—CH$_2$N(CH$_3$)$_2$,

—COOH,

—COO Alkyl of from 1 to 4 carbon atoms

—CH$_2$NH—C (CH$_3$) (CH$_2$OH)$_2$,

—CH$_2$—Morpholine,

—OCH$_2$—CO$_2$CH$_3$,

—OCH$_2$—CO$_2$C$_2$H$_5$, or

—O(CH$_2$)$_2$—N (C$_2$H$_5$)

in combination with one or more agents selected from the group consisting of:

(a) ACAT inhibitor;

(b) HMG-CoA reductase inhibitor;

(c) Lipid regulator; and (d) Bile acid sequestrant;

or a pharmaceutically acceptable salt thereof.

7. The method of claim 6 comprising the compound recited below:

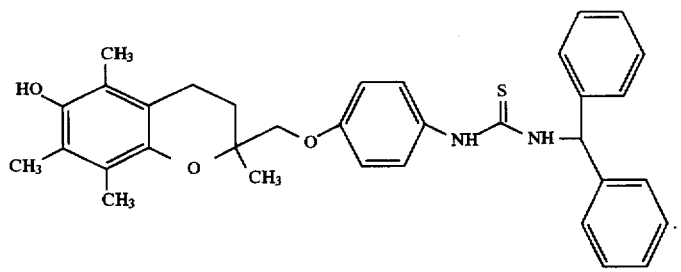

8. A method of inhibiting lipid oxidation in mammals in need thereof comprising administrating to such mammal an effective anti-oxidant amount of a compound of Formula I

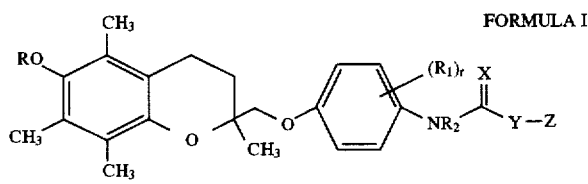
FORMULA I wherein:
R=Hydrogen or —CH$_2$—phenyl;
R$_2$=Hydrogen or lower alkyl of from 1–4 carbon atoms;
X=Oxygen or Sulfur;
Y=(CH$_2$)$_n$ or —NR' where R' is hydrogen, alkyl of from 1 to 12 carbon atoms or aryl of from 6 to 10 carbon atoms, or Z;

Z =
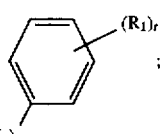

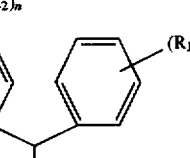

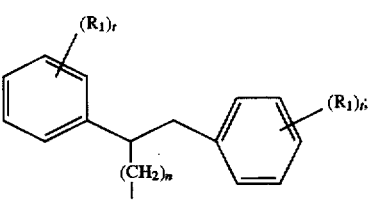

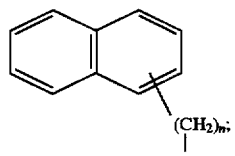

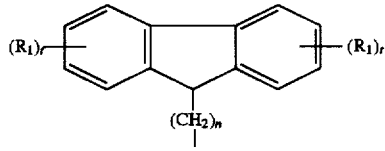

or —(CH$_2$)$_n$—alkyl of from 1 to 12 carbon atoms;
wherein n=0, 1 or 2;
t=0, 1, 2 or 3; and
R$_1$ is:
 hydroxy,
 halogen,
 —CF$_3$,
 —CN,
 —NH$_2$,
 —N(CH$_3$)$_2$,
 —CH$_2$N (CH$_3$)$_2$,
 —COOH,
 —COO Alkyl of from 1 to 4 carbon atoms,
 —CH$_2$NH—C (CH$_3$) (CH$_2$OH)$_2$,
 —CH$_2$—Morpholine,
 —OCH$_2$—CO$_2$CH$_3$,
 —OCH$_2$—CO$_2$C$_2$H$_5$, or
 —O(CH$_2$)$_2$—N (C$_2$H$_5$).

9. A method of inhibiting the expression of vascular cell adhesion molecule-1 (VCAM-1) comprising administering to a mammal in need thereof an effective inhibiting amount of a compound of Formula I:

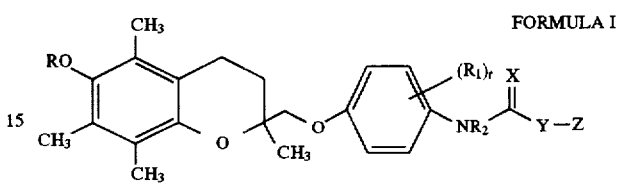
FORMULA I wherein:
R=Hydrogen or —CH$_2$— phenyl;
R$_2$=Hydrogen or lower alkyl of from 1–4 carbon atoms;
X=Oxygen or Sulfur;
Y=(CH$_2$)$_n$ or —NR' where R' is hydrogen, alkyl of from 1 to 12 carbon atoms or aryl of from 6 to 10 carbon atoms;

Z =
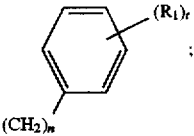

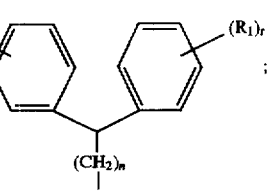

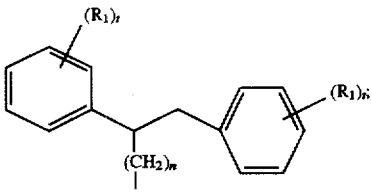

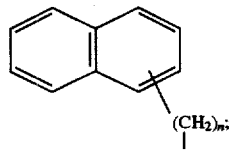

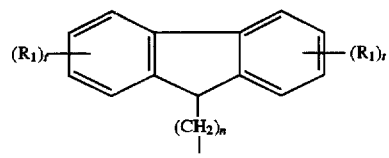

or —(CH$_2$)$_n$—alkyl of from 1 to 12 carbon atoms;
wherein n=0, 1 or 2;
t=0, 1, 2 or 3; and

27

R₁ is:
 alkyl of from 1 to 4 carbon atoms, hydroxy,
 alkoxy of from 1 to 4 carbon atoms, halogen,
 —CF₃,
 —CN,
 —NH₂,
 —N(CH₃)₂,
 —CH₂N(CH₃)₂,
 —COOH,
 —COO Alkyl of from 1 to 4 carbon atoms,
 —CH₂NH—C(CH₃)(CH₂OH)₂,
 —CH₂—Morpholine,
 —OCH₂—CO₂CH₃,
 —OCH₂—CO₂C₂H₅, or
 —O(CH₂)₂—N(C₂H₅)

or a pharmaceutically acceptable salt thereof.

10. A method for the treatment of inflammation in mammals in need thereof comprising administering to such mammal an effective amount of a compound of Formula I

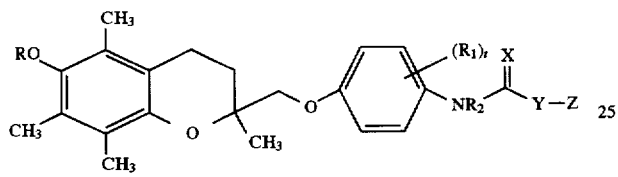

wherein:
 R=Hydrogen or —CH₂— phenyl;
 R₂=Hydrogen or lower alkyl of from 1–4 carbon atoms;
 X=Oxygen or Sulfur;
 Y=(CH₂)ₙ, —NR' where R' is hydrogen, alkyl of from 1 to 12 carbon atoms or aryl of from 6 to 10 carbon atoms, or Z;

Z =

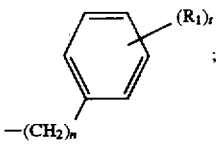

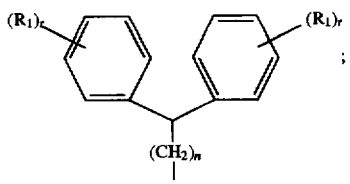

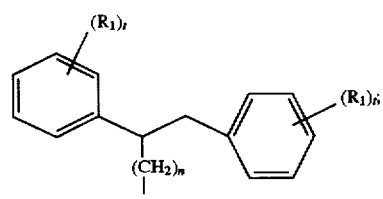

28

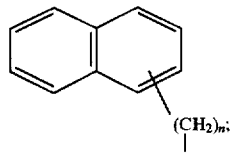

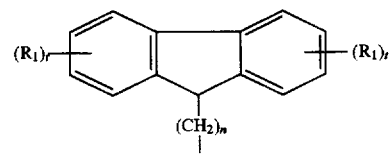

or —(CH₂)ₙ—alkyl of from 1 to 12 carbon atoms;

wherein n=0, 1 or 2, t=0, 1, 2 or 3; and

R₁ is:
 alkyl of from 1 to 4 carbon atoms, hydroxy,
 alkoxy of from 1 to 4 carbon atoms, halogen,
 —CF₃,
 —CN,
 —NH₂,
 —N(CH₃)₂,
 —CH₂N(CH₃)₂,
 —COOH,
 —COO Alkyl of from 1 to 4 carbon atoms,
 —CH₂NH—C(CH₃)(CH₂OH)₂,
 —CH₂—Morpholine,
 —OCH₂—CO₂CH₃,
 —OCH₂—CO₂C₂H₅, or
 —O(CH₂)₂—N(C₂H₅)

or a pharmaceutically acceptable salt thereof.

11. The method of claim 10 comprising the compound recited below:

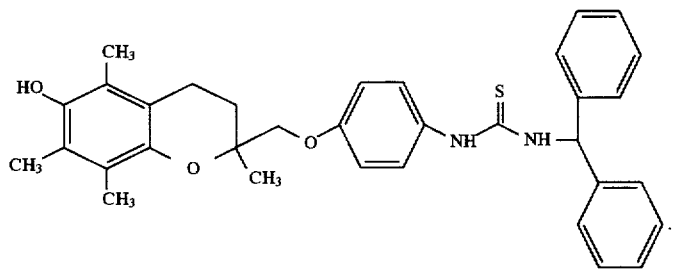

12. A pharmaceutical composition for the treatment of atherosclerosis in mammals in need thereof comprising a therapeutically effective amount of a compound in Formula I in admixture with a pharmaceutically acceptable excipient, diluent, or carrier:

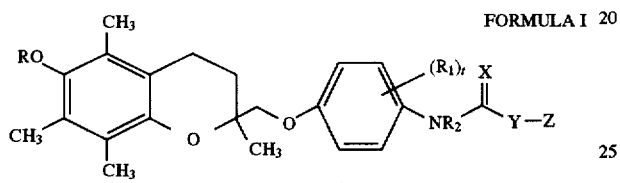

FORMULA I wherein

R=Hydrogen or —CH$_2$— phenyl;

R$_2$=Hydrogen or lower alkyl of from 1–4 carbon atoms;

X=Oxygen or Sulfur;

Y=(CH$_2$)$_n$ or —NR' where R' is hydrogen, alkyl of from 1 to 12 carbon atoms or aryl of from 6 to 10 carbon atoms, or Z;

Z =

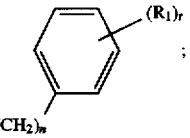

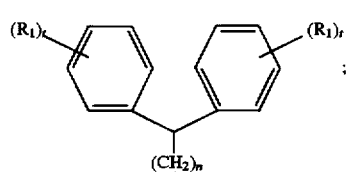

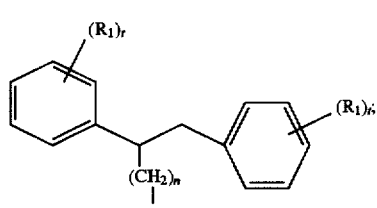

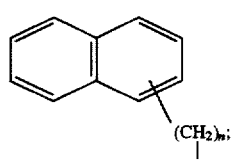

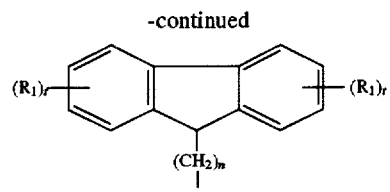

or —(CH$_2$)$_n$—alkyl of from 1 to 12 carbon atoms;

wherein n=0, 1 or 2;

t=0, 1, 2 or 3; and

R$_1$ is:

alkyl of from 1 to 4 carbon atoms, hydroxy, alkoxy of from 1 to 4 carbon atoms, halogen

CF$_3$,

—CN,

—NH$_2$,

—(CH$_3$)$_2$,

—CH$_2$N(CH$_3$)$_2$,

—COOH,

—COO Alkyl of from 1 to 4 carbon atoms

—CH$_2$NH—C(C$_3$H)(CH$_2$OH)$_2$,

—CH$_2$—Morpholine,

—OCH$_2$—CO$_2$CH$_3$,

—OCH$_2$—CO$_2$C$_2$H$_5$, or

—O(CH$_2$)$_2$—N(C$_2$H$_5$);

or a pharmaceutically acceptable salt thereof.

13. A pharmaceutical composition for the treatment of inflammation, atherosclerosis, restenosis, immune disorders, and transplant rejection in mammals in need thereof comprising administering to such mammal a therapeutically effective amount of a compound according to claim 8 in admixture with a pharmaceutically acceptable excipient, diluent, or carrier.

14. The composition of claim 13 comprising the compound recited below:

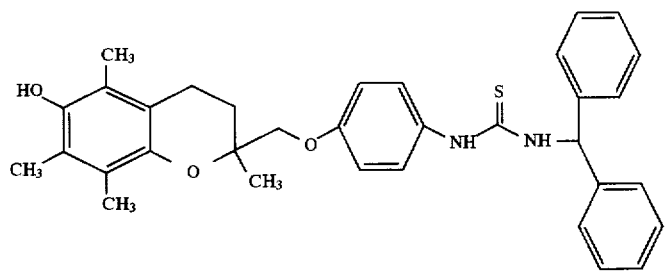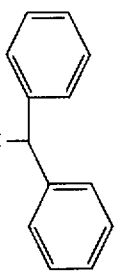

15. A compound having the structure in formula I:

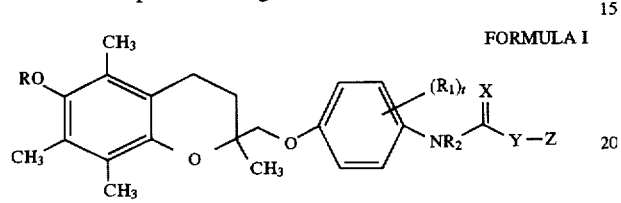
FORMULA I wherein:

R=Hydrogen or —CH$_2$— phenyl;

R$_2$=Hydrogen or lower alkyl of from 1–4 carbon atoms;

X=oxygen or Sulfur;

Y=(CH$_2$)$_n$ or —NR' where R' is hydrogen or aryl of from 6 to 10 carbon atoms, or Z;

Z =

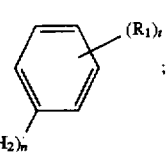

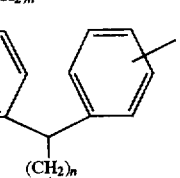

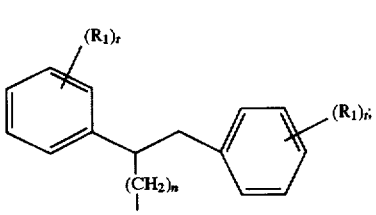

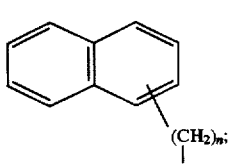

-continued

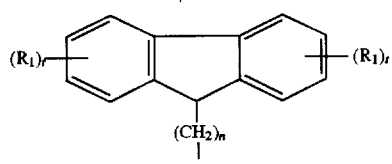

wherein n=0, 1 or 2;

t=0, 1, 2 or 3; and

R$_1$ is:

hydroxy, halogen,

—CF$_3$,

—CN,

—NH$_2$,

—N(CH$_3$)$_2$,

—CH$_2$N(CH$_3$)$_2$,

—COOH,

—COO Alkyl of from 1 to 4 carbon atoms,

—CH$_2$NH—C(CH$_3$)(CH$_2$OH)$_2$,

—CH$_2$—Morpholine,

—OCH$_2$—CO$_2$CH$_3$,

—OCH$_2$—CO$_2$C$_2$H$_5$, or

—O(CH$_2$)$_2$—N(C$_2$H$_5$).

16. The compound of claim 15 where R and R$_2$ are hydrogen, X is sulfur and Y is —NH—.

17. The compound of claim 15 of the structure:

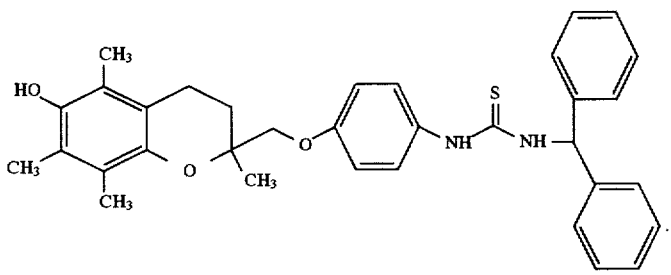

18. A compound selected from the group consisting of

1-Benzhydryl-3-[4—(6-hydroxy-2,5,7,8-tetramethyl-chroman-2-ylmethoxy)-phenyl]-thiourea 1-tert-Butyl-3-[4-(4-hydroxy-2,5,7,8-tetramethyl-chroman-2-ylmethoxy)-phenyl]-thiourea 1-[4-(6-Hydroxy-2,5,7,8-tetra-methyl-chroman-2-ylmethoxy)-phenyl]-3-naphthalen-2-yl-thiourea 1-Benzhydryl-3-[4-(6-hydro 7,8-tetramethyl-chroman-2-ylmethoxy)-phenyl]-urea 1-Dodecyl-3-[4-(6-hydroxy-2,5,7,8-tetramethyl-chroman-2-ylmethoxy)-phenyl]-thiourea 1-Benzyl-3-[4-(6-hydroxy-2,5,7,8-tetramethyl-chroman-2-ylmethoxy)-phenyl]-thiourea 1-Benzhydryl-3-[4-(6-benzyloxy-2,5,7,8-tetramethyl-chroman-2-ylmethoxy)-phenyl]-thiourea 3-[4-(6-hydroxy-2,5,7,8-tetra-methyl-chroman-2-ylmethoxy)-1,1-phenyl]-diphenyl-urea 1-(1,2-Diphenyl-ethyl)-3-[4-(6-hydroxy-2,5,7,8-tetramethyl-chroman-2-ylmethoxy)-phenyl]-thiourea 1-[4-(6-Hydroxy-2,5,7,8-tetramethyl-chroman-2-ylmethoxy)-phenyl]-3-(phenyl-p-tolyl-methyl)-thiourea 1-[4-(6-Hydroxy-2,5,7,8-tetramethyl-chroman-2-ylmethoxy)-phenyl]-3-(isopropyl-phenyl)-thiourea 1-(2,2-Diphenyl-ethyl)-3-[4-(6-hydroxy-2,5,7,8-tetramethyl-chroman-2-ylmethoxy)-phenyl]-thiourea 1-[(4-Chloro-phenyl)-phenyl-methyl]-3-[4-(6-hydroxy-2,5,7,8-tetramethyl-chroman-2-ylmethoxy)-phenyl]-thiourea 1-[4-(6-Hydroxy-2,5,7,8-tetramethyl-chroman-2-ylmethoxy)-phenyl]-3-(3-methoxy-phenyl)-thiourea N-[4-[[3,4-dihydro-2,5,7,8-tetra-methyl-6-(phenylmethoxy)-2H-1-benzopyran-2-yl]methoxy]phenyl-[2-(1,1-dimethylethyl)-6-methyl-phenyl]urea N-[4-[[3,4-dihydro-6-hydroxy-2,5,7,8-tetra-methyl-2H-1-benzopyran-2-yl)methoxy]phenyl]-N'-methylthiourea, and N-[4-[[3,4-dihydro-6-hydroxy-2,5,7,8-tetra-methyl-6-(phenylmethoxy)-2H-1-benzopyran-2-yl]methoxy]phenyl]-N/-[2-(1-methylethyl)phenyl]urea.

19. A process for producing a compound of formula I

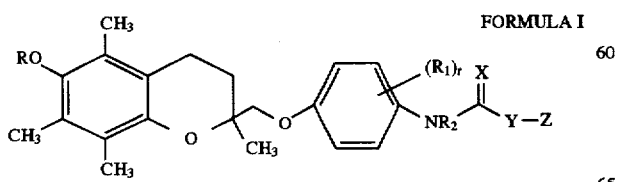

FORMULA I wherein:

R=Hydrogen or —CH₂— phenyl;

R₂=Hydrogen or lower alkyl of from 1–4 carbon atoms;

X=Oxygen or Sulfur;

Y=(CH₂)$_n$ or —NR' where R' is hydrogen, alkyl of from 1 to 12 carbon atoms or aryl of from 6 to 10 carbon atoms, or Z;

Z=

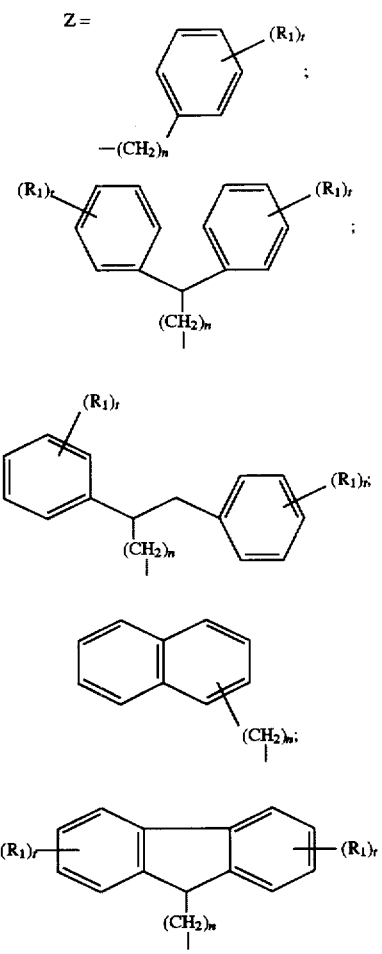

or(CH₂)$_n$—alkyl of from 1 to 12 carbon atoms;

wherein n=0, 1 or 2;

t=0, 1, 2 or 3; and

R₁ is:

alkyl of from 1 to 4 carbon atoms, hydroxy, alkoxy of from 1 to 4 carbon atoms, halogen,

—CF₃,

—CN,

—NH₂,

—N(CH$_3$)$_2$,
—CH$_2$N(CH$_3$)$_2$,
—COOH,
—COO Alkyl of from 1 to 4 carbon atoms,
—CH$_2$NH—C(CH$_3$)(CH$_2$OH)$_2$,
—CH$_2$—Morpholine,
—OCH$_2$—CO$_2$CH$_3$,
—OCH$_2$—CO$_2$C$_2$H$_5$, or
—O(CH$_2$)$_2$—N(C$_2$H$_5$);
comprising reacting a compound of Formula II
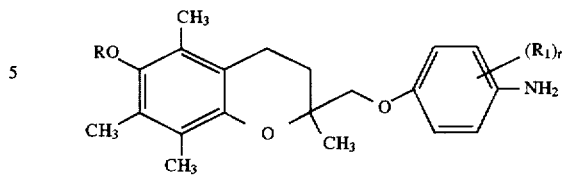
with Z—NC(X) or Z—C(X)Cl.
* * * * *